US010907193B2

(12) United States Patent
Suliman et al.

(10) Patent No.: US 10,907,193 B2
(45) Date of Patent: Feb. 2, 2021

(54) METHODS AND SYSTEMS FOR THE DETECTION OF RICIN AND OTHER RIBOSOME INACTIVATING PROTEINS

(71) Applicant: SRC, Inc., North Syracuse, NY (US)

(72) Inventors: Huda Sirageldin Suliman, North Syracuse, NY (US); Stacey Ann Massulik, Syracuse, NY (US); Frances Louise Stites, Ashburn, VA (US); Timothy Francis Moshier, Fulton, NY (US); Kenton Arthur Doctor, East Syracuse, NY (US); Jeffrey Harold Mills, Liverpool, NY (US); Lisa Helen Chamberlin, East Syracuse, NY (US)

(73) Assignee: ACUMEN DETECTION, LLC, North Syracuse, NY (US)

( * ) Notice: Subject to any disclaimer, the term of this patent is extended or adjusted under 35 U.S.C. 154(b) by 0 days.

(21) Appl. No.: 13/898,917

(22) Filed: May 21, 2013

(65) Prior Publication Data

US 2014/0065623 A1 Mar. 6, 2014

Related U.S. Application Data

(60) Provisional application No. 61/649,418, filed on May 21, 2012.

(51) Int. Cl.
*G01N 33/542* (2006.01)
*C12Q 1/6806* (2018.01)
*C12Q 1/68* (2018.01)

(52) U.S. Cl.
CPC .......... *C12Q 1/6806* (2013.01); *C12Q 1/68* (2013.01); *G01N 33/542* (2013.01); *C12Q 2525/119* (2013.01); *C12Q 2565/1015* (2013.01); *G01N 2333/42* (2013.01)

(58) Field of Classification Search
CPC ............... C12Q 2525/119; C12Q 2565/1015
See application file for complete search history.

(56) References Cited

U.S. PATENT DOCUMENTS

| | | | |
|---|---|---|---|
| 6,864,056 B1 | 3/2005 | Davies et al. | |
| 7,172,861 B2 | 2/2007 | Keener et al. | |
| 7,745,136 B1* | 6/2010 | Dorsey | C12Q 1/6804 435/6.16 |
| 8,088,976 B2* | 1/2012 | Boukharov | C07K 14/4354 800/285 |
| 2006/0240447 A1* | 10/2006 | Czajka | C12Q 1/6895 435/6.16 |
| 2008/0050725 A1* | 2/2008 | Keener | 435/6 |
| 2010/0279295 A1* | 11/2010 | Roy | C12Q 1/6844 435/6.12 |
| 2010/0291553 A1* | 11/2010 | Nakagawa | 435/6 |
| 2011/0053146 A1 | 3/2011 | Schramm et al. | |

FOREIGN PATENT DOCUMENTS

| | | | |
|---|---|---|---|
| CN | 101980023 | 2/2011 | |
| EP | 1241267 A2 * | 9/2002 | ....... C12Q 2521/301 |
| WO | WO 2008105796 A2 * | 9/2008 | ............... C12Q 1/34 |

OTHER PUBLICATIONS

Srivatsan, SG., et al. A highly emissive fluorescent nucleoside that signals the activity of toxic ribosome inactivating proteins. Angew. Chem. Int., vol. 47, p. 6661-6665, 2008.*
Wang, YX., et al. Solution structure of anti-HIV-1 and anti-tumor preotein MAP30: structural insights into its multiple functions. Cell, vol. 99, p. 433-442, 1999.*
English translation of the Description of EP 1241267 A2, pp. 1-32 (Year: 2002).*
Nicolas, E. et al., A New Class of Dna Glycosylase/Apurinic/Apyrimidinic Lyases That Act on Specific Adenines in Single-Stranded DNA. J. Biol. Chem., vol. 273, pp. 17216-17220 (Year: 1998).*
Ogasawara, T. et al., A new class of enzyme acting on damaged ribosomes: ribosomal RNA apurinic site specific lyase found in wheat germ, The EMBO J., vol. 18, pp. 6522-6531 (Year: 1999).*
Endo, Y. et al., The RNA N-Glycosylase Activity of Ricin A-chain, J. Biol. Chem., vol. 263, pp. 8735-8739 (Year: 1988).*
Lubelli et al. "Detection of Ricin and other Ribosome-inactivating Proteins by an Immuno-polymerase Chain Reaction Assay" Anal. Biochem., 2006, 355(1), pp. 102-109.
Fulton et al. "Fluorogenic Hand-held Immunoassay for the Identification of Ricin: Rapid analyte measurement platform." J. Immunoass. Immunochem., 2007, 28, pp. 227-241.
Lockett et al. "Molecular Beacon-style Hybridization Assay for Quantitative Analysis of Surface Invasive Cleavage Reactions" Anal. Chem., 2007, 79(15), pp. 6031-6036.
Manganelli et al. "Real Time PCR Using Molecular Beacons: A new tool to identify point mutations and to analyze gene expression in mycobacterium tuberculosis" Methods Mol. Med., 2001, 54, pp. 295-310.
Melchior, Jr. et al. "A Functional Quantitative Polymerase Chain Reaction Assay for Ricin, Shiga toxin, and Related Ribosome-inactivating Proteins" Anal. Biochem., 2010, 396(2), pp. 204-211.

(Continued)

*Primary Examiner* — Teresa E Strzelecka

(74) *Attorney, Agent, or Firm* — Bond Schoeneck & King, PLLC; George McGuire

(57) ABSTRACT

A device, method, and system for the detection of ribosome inactivating protein activity, including the ricin toxin, in a sample. According to one embodiment, the ribosome inactivating protein in the sample removes an adenine from a labeled DNA substrate to create an abasic site. An AP lyase can then cleave the DNA substrate at the abasic site, allowing the fluorophore located at or near one end of the DNA substrate and the quencher at or near the other end of the DNA substrate to spatially separate. Once the fluorophore and the quencher are sufficiently separated, the fluorophore will emit a fluorescence signal. Increasing fluorescence, indicating ribosome inactivating protein activity, will be monitored in real time using a detection system.

5 Claims, 8 Drawing Sheets

Specification includes a Sequence Listing.

(56) References Cited

OTHER PUBLICATIONS

Pierce et al. "Development of Quantitative RT-PCR Assay to Examine the Kinetics of Ribosome Depurination by Ribosome Inactivating Proteins Using *Saccharomyces cerevisiae* as a Model" RNA, 2011, 17(1), pp. 201-210.
Roday et al. "Detection of an Abasic Site in RNA with Stem-loop DNA Beacons: Application to an activity assay for ricin toxin a-chain" J. Biochem. Biophys. Methods, 2008, 70(6), pp. 945-953.
International Search Report Form PCT/ISA/220, International Application No. PCT/IB2013/001639, pp. 1-6, dated Dec. 4, 2014.

* cited by examiner

METHODS AND SYSTEMS FOR THE DETECTION OF RICIN AND OTHER RIBOSOME INACTIVATING PROTEINS

CROSS-REFERENCE TO RELATED APPLICATIONS

This application claims priority to U.S. Provisional Patent Application Ser. No. 61/649,418, filed on May 21, 2012 and entitled "Fluorescence Assay for Detection of Ricin and Other Ribosome Inactivating Proteins," the entire disclosure of which is incorporated herein by reference.

BACKGROUND OF THE INVENTION

1. Field of the Invention

The present invention relates to the detection of ricin and other ribosome inactivating proteins and, more specifically, to a fluorescence assay for the detection of ricin and other ribosome inactivating proteins.

2. Description of the Related Art

Ricin is a potent protein toxin produced by the castor oil plant *Ricinus communis*. Ricin is a 66 kDa ribosome inactivating protein ("RIP") composed of an A chain and B chain linked by a disulfide bond. The 32 kDa B chain binds galactose residues on the surface of the cell, which results in internalization of the ricin. Once inside the cell, the 34 kDa A chain dissociates from the B chain and translocates into the cytosol where it performs its enzymatic activity. Ricin A chain acts by removing a specific adenine (A4324) from ribosomal RNA, thereby inhibiting protein synthesis by the ribosomes and causing cell death. The natural substrate for Ricin is the well-conserved "Sarcin-Ricin Loop" of the 28S eukaryotic ribosomal RNA, which is normally used to bind elongation factors during protein synthesis. Ricin is extremely toxic if inhaled, injected, or ingested, with a dose the size of a few grains of table salt capable of killing an adult human. Due to this extreme lethality, and due to the ease of purification from the castor seed, ricin has been and continues to be used as a biological weapon. As a result, there is a continued need for systems and methods for the detection of ricin. In addition to ricin detection, there is similarly a continued need for rapid, efficient, and affordable detection of other ribosome inactivating proteins, including but not limited to Shiga toxins, trichosanthin, luffin, abrin, and saporin.

Existing ricin detection assays, including Enzyme Linked Immunosorbent Assays ("ELISA") and cell free translation systems, are complex, time consuming, expensive, and more suitable for laboratory analysis. Many in-vitro assays use synthetic mimics of the targeted sarcin-ricin loop, but because of the secondary structure these substrates require a final melting and annealing step for detection. This type of endpoint assay is not ideal for use in fieldable detection systems and there is a continued need for an assay for the rapid detection of Ricin activity in real time.

BRIEF SUMMARY OF THE INVENTION

According to a first aspect is a method for detecting the presence of a ribosome inactivating protein target in a sample, wherein the ribosome inactivating protein target is capable of interacting with a nucleic acid substrate to create an abasic site, the method comprising the steps of: (i) adding the sample to a reaction mixture to create a second mixture, wherein the reaction mixture comprises an AP lyase and a plurality of molecules of the nucleic acid substrate, wherein said nucleic acid substrate comprises a target sequence, a fluorophore, and a quencher; (ii) incubating said second mixture under conditions sufficient for the ribosome inactivating protein target to create an abasic site in the nucleic acid substrate at the target sequence and for the AP lyase to cleave the created abasic site, wherein, if said ribosome inactivating protein target is present in said sample, said fluorophore and said quencher dissociate and said fluorophore produces a notification signal; and (iii) detecting said notification signal, wherein said signal indicates the presence of said ribosome inactivating protein target in said sample.

According to an aspect, the ribosome inactivating protein target is ricin and the nucleic acid substrate is selected from the group consisting of: dsDNA, ssDNA, RNA, oligonucleotides, chimeric nucleic acids, and combinations thereof. According to another embodiment, the nucleic acid substrate further comprises a non-nucleic acid component. The target can comprise, for example, the sarcin-ricin loop.

According to another aspect, the notification signal is detected in real time via a fluorescence based detection system, for example, a quantitative PCR platform.

According to a second aspect is a system for detecting the presence of a ribosome inactivating protein target in a sample, wherein the ribosome inactivating protein target is capable of interacting with a nucleic acid substrate to create an abasic site, the system comprising: (i) a sample, said sample potentially comprising said target; (ii) a reaction mixture comprising an AP lyase and a plurality of molecules of the nucleic acid substrate, wherein said nucleic acid substrate comprises a target sequence, a fluorophore and a quencher, wherein when said sample is added to the reaction mixture to create a second mixture and the second mixture is incubated under conditions sufficient for the ribosome inactivating protein target to create an abasic site in the nucleic acid substrate and for the AP lyase to cleave the created abasic site, said fluorphore produces a notification signal; and (iii) a sensor, wherein said sensor is configured to detect said notification signal, the detection of said notification signal indicating the presence of said ribosome inactivating protein target in said sample.

According to an aspect of the system, the ribosome inactivating protein target is ricin and the nucleic acid substrate is selected from the group consisting of: dsDNA, ssDNA, RNA, oligonucleotides, chimeric nucleic acids, and combinations thereof. According to another embodiment, the nucleic acid substrate further comprises a non-nucleic acid component. The target can comprise, for example, the sarcin-ricin loop.

According to another aspect of the system, the notification signal is detected in real time via a fluorescence based detection system, for example, a quantitative PCR platform.

According to a third aspect is a method for detecting the presence of ricin in a sample, the method comprising the steps of: (i) adding the sample to a reaction mixture to create a second mixture, wherein the reaction mixture comprises an AP lyase and a DNA substrate, wherein the DNA substrate comprises a fluorophore and a quencher; (ii) incubating the second mixture under conditions sufficient for the ricin to create an abasic site in the DNA substrate and for the AP lyase to cleave the created abasic site, wherein, if ricin is present in said sample, said fluorophore and said quencher dissociate and said fluorophore produces a notification signal; and (iii) detecting said notification signal, wherein said signal indicates the presence of ricin in said sample.

According to another aspect, the DNA substrate is a synthesized nucleic acid. According to another embodiment, the DNA substrate comprises a sarcin-ricin loop, and/or comprises a non-nucleic acid component.

According to another aspect of the method, the notification signal is detected in real time via a fluorescence based detection system, for example, a quantitative PCR platform.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 5:
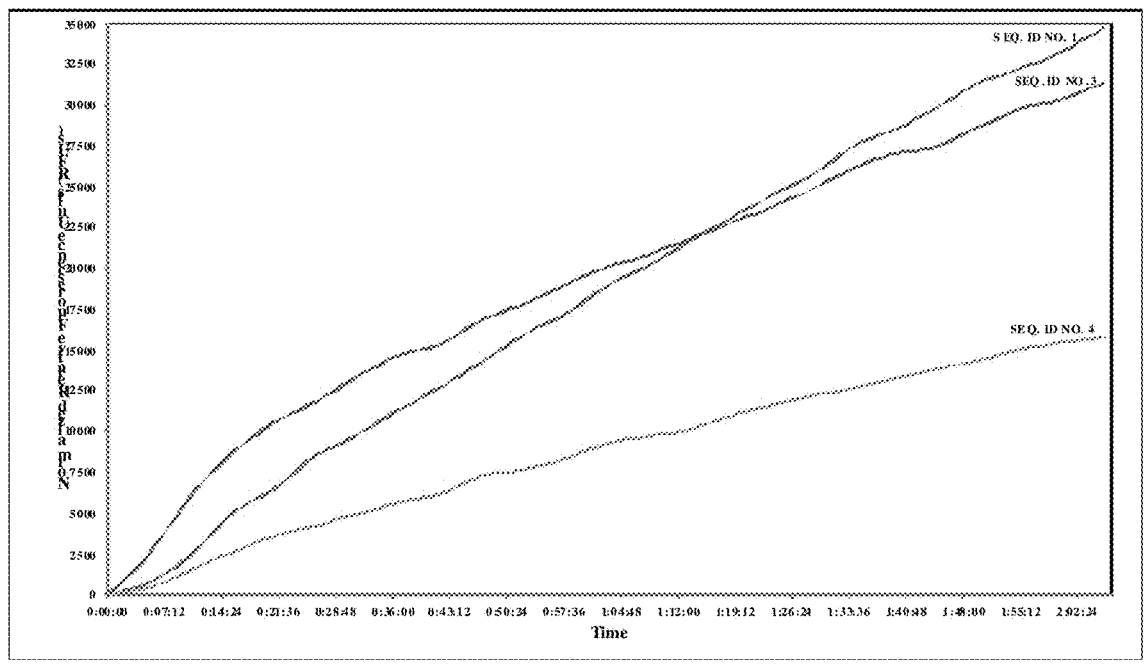
Figure 6A:
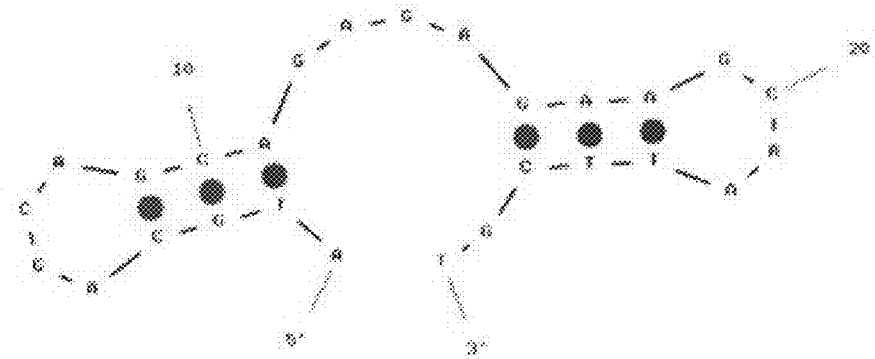
Figure 6B:
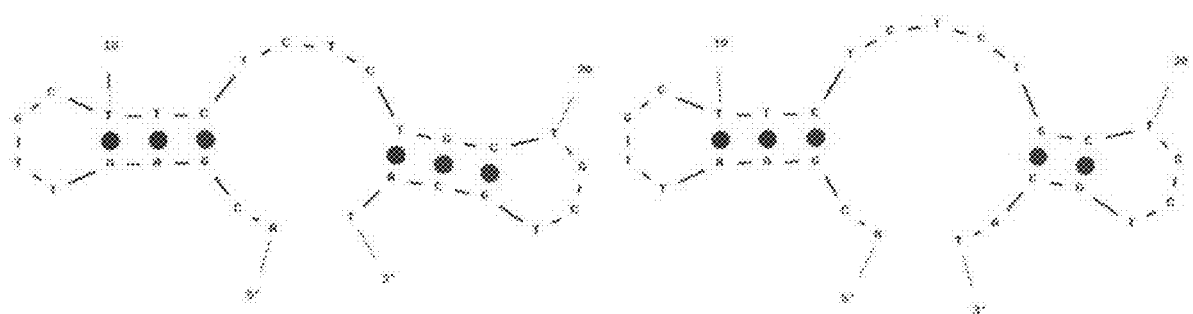
Figure 6C:
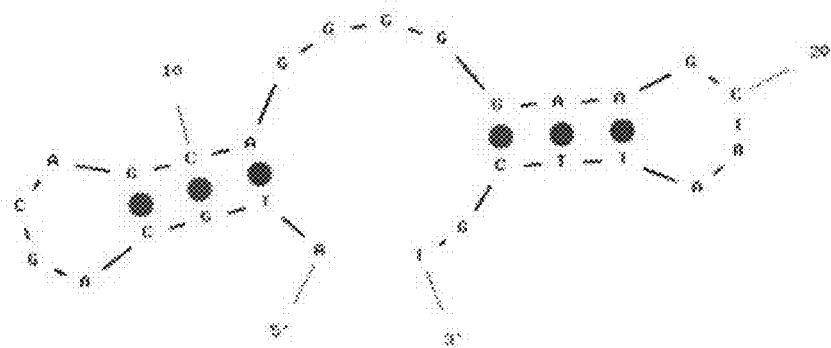

FIG. 5 is a graph comparing the performance of three different substrates (SEQ. ID NO. 1, SEQ. ID NO. 3, and SEQ. ID NO. 4) using ricin A chain in a fluorometer according to an embodiment;

FIGS. FIGS. 6A, 6B, and 6C are representative diagrams showing the secondary structure of the following three substrates: SEQ. ID NO. 1 (FIG. 6A), SEQ. ID NO. 3 (FIG. 6B), and SEQ. ID NO. 4 (FIG. 6C), according to an embodiment;

FIG. 7 is a graph showing the activity of ricin A chain using the SEQ. ID NO. 1 substrate in a fluorometer according to an embodiment;

FIG. 8 is a graph showing the limit of detection using the SEQ. ID NO. 1 substrate and ricin A chain in a fluorometer according to an embodiment;

FIG. 9 is a graph showing the activity of ricin A chain using SEQ. ID NO. 2 in the RAZOR™ EX. according to an embodiment;

FIG. 10 is a graph showing the activity of ricin toxin using SEQ. ID NO. 1 in a fluorometer according to an embodiment; and FIG. 11 is a graph showing the activity of ricin A chain and ricin toxoid using SEQ. ID NO. 1 in a fluorometer.

DETAILED DESCRIPTION OF THE INVENTION

According to one embodiment is a method and assay utilizing a DNA substrate labeled on one end with a fluorophore and labeled on the other end with a quencher. The ricin or other RIP target will remove the adenine or other base from the labeled substrate to thereby create an abasic site, followed by cleavage at the abasic site by a lyase. This will allow the fluorophore and the quencher to spatially separate emitting a fluorescence signal. The fluorescence signal will be monitored in real time, tracking the enzymatic activity of the toxin. This assay can also be used to detect RIPs other than and in addition to the ricin toxin.

Referring now to the drawings, wherein like reference numerals refer to like parts throughout, there is seen in FIG. 1 a flowchart of a method for the detection of ricin and other ribosome inactivating proteins using a fluorescence assay according to an embodiment. At step 10, a sample is added to a reaction mixture. The sample can be obtained from anyone or anything, including from land, water, or air in a particular location. Obtaining samples for analysis is well-known in the art. FIG. 2 is a representative ribbon diagram of the full ricin toxin consisting of the A and B chains. FIG. 3 is a molecular diagram representing the removal of an adenine from a target DNA substrate (labeled with a fluorophore (6FAM™) and a quencher (BHQ™1)) by ricin A chain creating an abasic site. Subsequently, the AP lyase cleaves the abasic site created by ricin A chain, allowing for the spatial separation of the fluorophore and quencher causing an emitted fluorescence signal. The increase in fluorescence may be monitored by an appropriate temperature controlled fluorescence reader, including but not limited to a FilterMax® F5 fluorometer, a Genedrive®, a RAZOR™ EX, or a Rotor-Gene® Q system.

Accordingly to one embodiment, the assay was developed using recombinant ricin A chain from BEI Resources (Manassas, Va.) and later re-analyzed using ricin toxin from BEI Resources (Manassas, Va.). Ricin toxoid (chemically inactivated ricin toxin) from BEI Resources (Manassas, Va.) was used to confirm the specificity of the assay to ricin activity in the studies. The ricin A chain is commonly used for research purposes and has full biological activity (see FIG. 2). It is noted in the literature that the ricin A chain is able to remove adenines from both natural and synthetic substrates. According to an embodiment, the studies were performed using designed and synthesized fluorescently labeled nucleotide substrates (SEQ. ID NO. 1 through 12) with the 6-FAM™/BHQ™1 fluorophore/quencher pair or the Alexa Fluor® 488/BHQ™1 fluorophore/quencher pair (see Table 1). Experimental conditions also included sodium citrate tribasic dihydrate purchased from Sigma-Aldrich (Saint Louis, Mo.), citric acid monohydrate purchased from Sigma-Aldrich (Saint Louis, Mo.), and Endonuclease VIII purchased from New England Biolabs (Ipswich, Mass.).

TABLE 1

Synthesized fluorescent nucleotide substrates

| Name | Sequence (5' to 3') |
|---|---|
| SEQ. ID NO. 1 | (6FAM ™)-ATGCAGCAGCAGAGAGAAGCAATTCGT-(BHQ ™1) |
| SEQ. ID NO. 2 | (Alexa Fluor ® 488)-ATGCAGCAGCAGAGAGAAGCAATTCGT-(BHQ ™1) |
| SEQ. ID NO. 3 | (6FAM ™)-ACGAATTGCTTCTCTCTGCTGCTGCAT-(BHQ ™1) |
| SEQ. ID NO. 4 | (6FAM ™)-ATGCAGCAGCAGGGGGAAGCAATTCGT-(BHQ ™1) |

TABLE 1-continued

Synthesized fluorescent nucleotide substrates

| Name | Sequence (5' to 3') |
|---|---|
| SEQ. ID NO. 5 | (6FAM™)-ATGCATGCAGCAGAGAGAAGCAATTCGT-(BHQ™1) |
| SEQ. ID NO. 6 | (6FAM™)-AAAAAAAAAAAGAGAAAAAAAAAAAA-(BHQ™1) |
| SEQ. ID NO. 7 | (6FAM™)-AAAAAAAGAAAGAGATTACAAAAAAA-(BHQ™1) |
| SEQ. ID NO. 8 | (6FAM™)-AAAAAAAAAAGGAGACTAAAAAAAAA-(BHQ™1) |
| SEQ. ID NO. 9 | (6FAM™)-ATGCCTCCAGCAGAGAAGCAATTCGT-(BHQ™1) |
| SEQ. ID NO. 10 | (6FAM™)-TGCTCCTAGTACGAGAGGACCGGAGTG-(BHQ™1) |
| SEQ. ID NO. 11 | (6FAM™)-ATGCAGCAGCAGUGAGAAGCAATTCGT-(BHQ™1) |
| SEQ. ID NO. 12 | (6FAM™)-CCTGCTAGCAGACGAGAGGAGCAATTGCTTG-(BHQ™1) |

In Table 1, (6FAM™)=6-Carboxyfluorescein (or other fluorophore), (Alexa Fluor® 488)=one of a family of fluorophores produced by Invitrogen (Grand Island, N.Y.) (or other fluorophore), and (BHQ™1)=black hole Quencher™ 1 (or other quencher). Other modifications are possible.

According to an embodiment of the present invention, the substrate is, for example, anything capable of being acted upon by RIP activity, including but not limited to DNA (including isolated and genomic), dsDNA, ssDNA, RNA, oligonucleotides, and chimeric nucleic acids (e.g., containing single stranded and double stranded regions, or comprising both RNA and DNA), as well as molecules comprising both a nucleic acid such as RNA and/or DNA together with one or more non-nucleic acid components, molecules, or elements, among many other types of substrates. According to one embodiment, the substrate is DNA that contains, for example, at least one GAG sequence, since this sequence has been shown to be the smallest substrate for ricin A chain. Alternatively, the substrate can contain at least a GAGA sequence, or can contain any target sequence depending upon the target to be detected. The substrate can similarly comprise multiple target sequences for detection of multiple targets. In yet another embodiment, the substrate can be a very long DNA molecule comprising a plurality of target and/or non-target sequences. Studies were performed using designed and synthesized fluorescently labeled nucleotide substrates (SEQ. ID NOS. 1 through 12) with the 6-FAM™/BHQ™1 fluorophore/quencher pair or the Alexa Fluor® 488/BHQ™1 fluorophore/quencher pair (Table 1). Accordingly, the reaction mixture preferably contains a substrate, as described above, labeled with a fluorophore located on, at, or in proximity to one end of the molecule and a quencher located on, at, or in proximity to the opposite or another end of the molecule. An Alexa Fluor® 488/BHQ™1 fluorophore/quencher pair as described herein worked preferably for the fieldable instrument such as the RAZOR™ EX, and both worked for the FilterMax® F5. However, many other fluorophore/quencher pairs will be possible and/or even preferable depending on the platform used and/or the experimental conditions.

Figure 1:
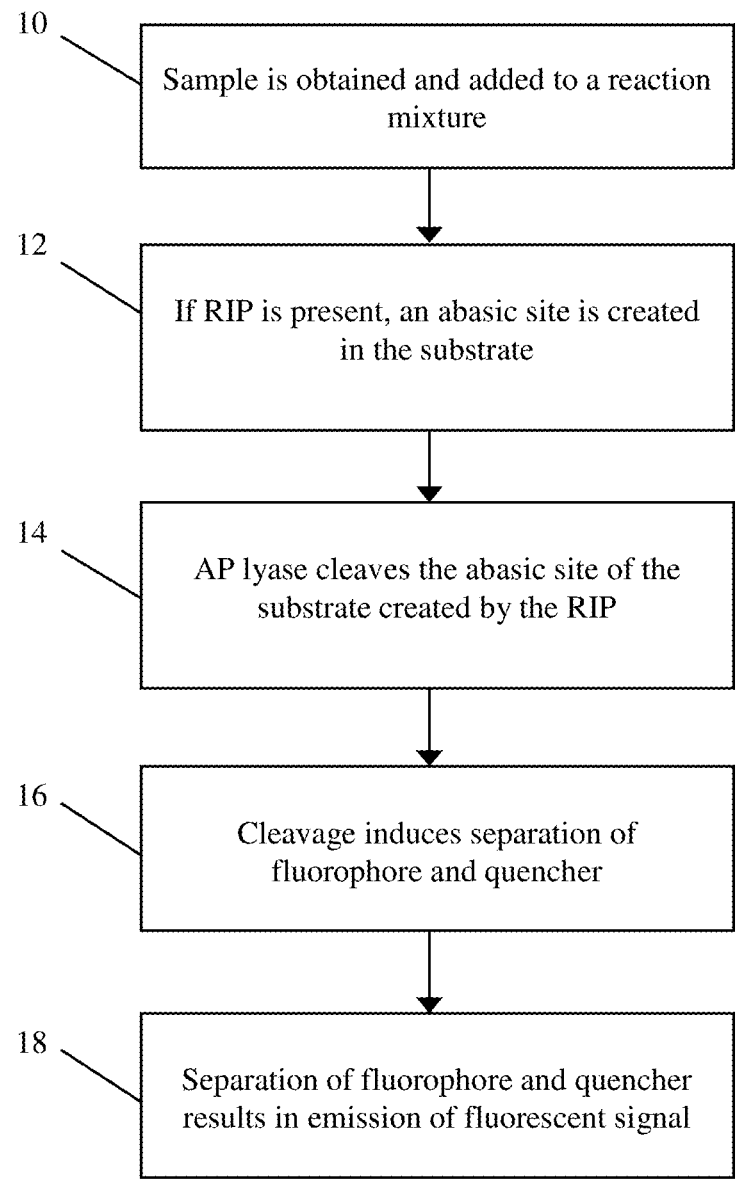
FIG. 1 is flowchart of a method for the detection of ricin and other ribosome inactivating proteins using a fluorescence assay according to an embodiment.
Figure 2:
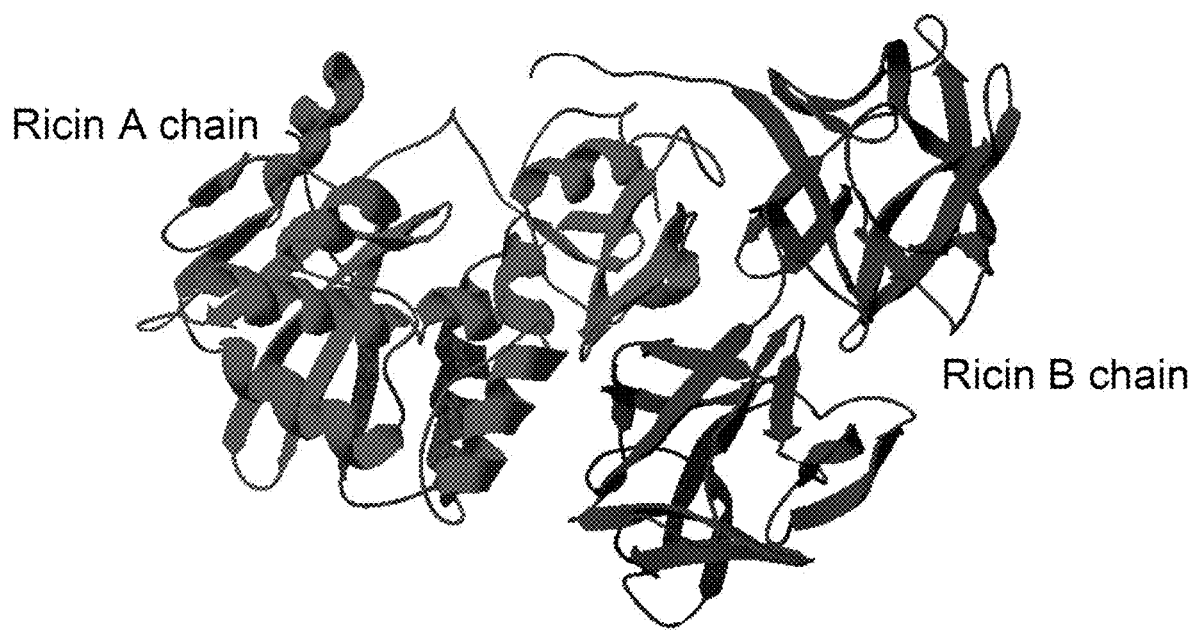
FIG. 2 is a representative ribbon diagram of the full structure of the Ricin toxin.
Figure 3:
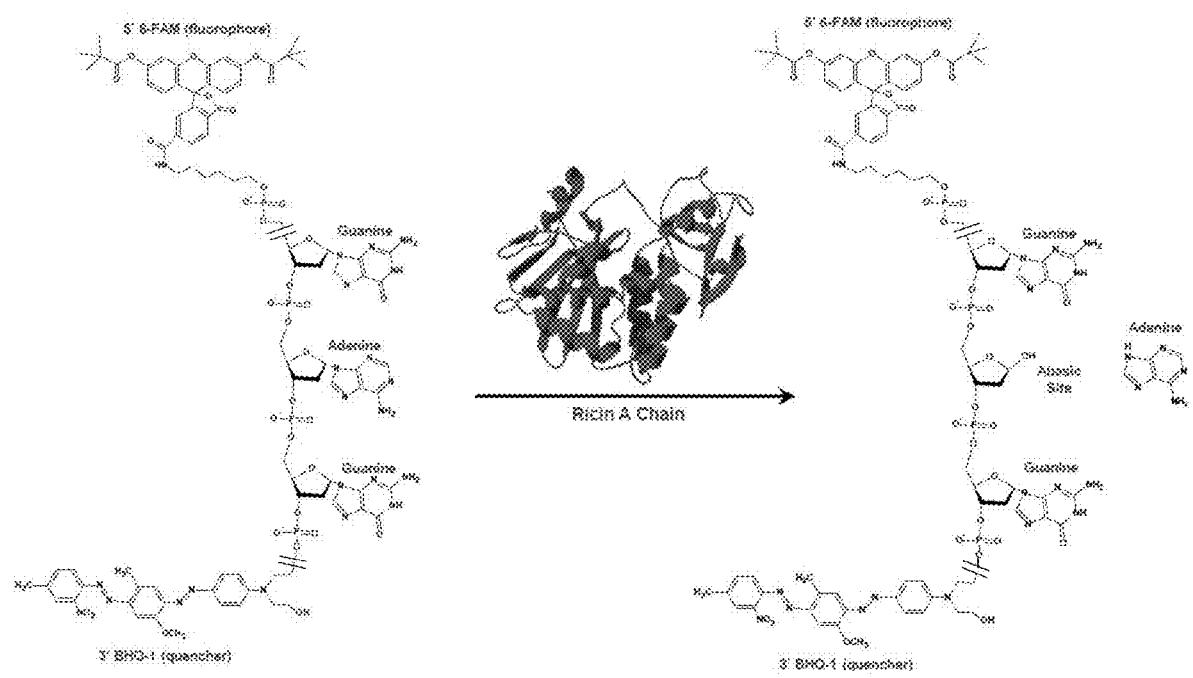
FIG. 3 is a representative molecular diagram of the removal of an adenine from a target substrate by the Ricin A chain, where the DNA substrate is labeled with a fluorophore (6-FAM) and a quencher (BHQ-1) according to an embodiment.
Figure 4:
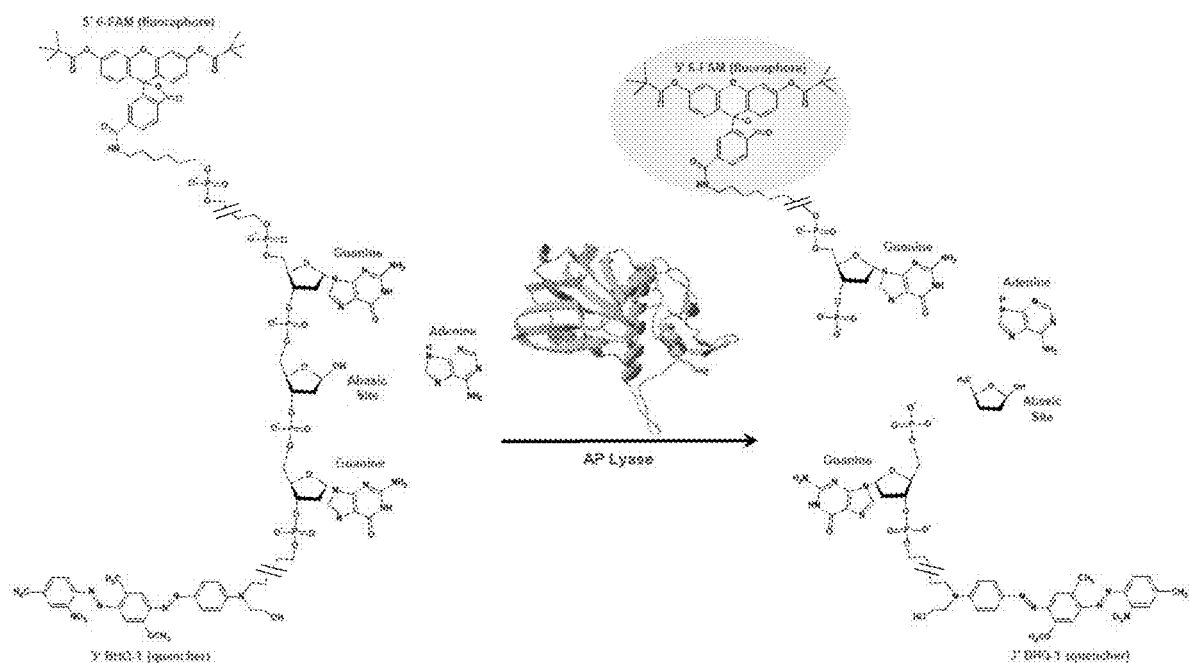
FIG. 4 is a representative molecular diagram depicting cleaving of the abasic site of the substrate (after the adenine has been removed by the Ricin A chain as depicted in FIG. 3) by AP lyase, and the subsequent separation of the fluorophore and quencher which allows the fluorophore to emit a fluorescent signal, according to an embodiment.

At step 12 of the method, if the target (ricin or another RIP, for example) is present in the sample then the target will act on the substrate by removing an adenine from the substrate (such as the GAG sequence), thereby creating an abasic site (also known as an AP (apurinic/apyrimidinic) site) wherein the purine or pyrimidine base is absent, but will not cleave through the entire DNA molecule. See, for example, FIG. 3.

According to one embodiment, substrate design began by studying the natural target for ricin, namely the sarcin-ricin loop of the 28S eukaryotic ribosomal RNA. Elements from the sarcin-ricin loop, including but not limited to the GAG sequence, were initially incorporated into the design of synthetic DNA substrates (Table 1). Other versions of substrates were also designed and synthesized (Table 1). The performance of some synthesized substrates seemingly depended on structure in addition to or independent of sequence. FIG. 5 is a graphical representation comparing the performance of SEQ. ID NO. 1 to SEQ. ID NO. 3 and SEQ. ID NO. 4. SEQ. ID NO. 1 has similar performance to SEQ. ID NO. 3. Although SEQ. ID NO. 3 does not have a GAGA or GAG sequence, it has a similar shape to SEQ. ID NO. 1 (shown in FIG. 6). SEQ. ID NO. 4 did not perform as well as SEQ. ID NO. 1. SEQ. ID NO. 4 is the same sequence as SEQ. ID NO. 1, except that the GAGA sequence is replaced with GGGG. Both SEQ. ID NO. 1 and SEQ. ID NO. 4 have the same shape. Therefore, shape and sequence seem to both play a role in catalysis by ricin of the designed substrates. These structures may mimic the GAGA tetraloop found in the sarcin-ricin loop of the 28S eukaryotic ribosomal RNA.

At step 14 of the method the substrate, as modified by the target, is then cleaved. According to one embodiment, an apurinic/apyrimidinic (AP) lyase—including but not limited to a lyase such as Endonuclease VIII—present in the reaction mixture (or added at a subsequent step) cleaves the abasic site in the DNA created by the ricin or another ribosome inactivating protein in the sample. See, for example, FIG. 4. AP lyases are enzymes that function in DNA repair and specifically target abasic sites. AP lyases usually target abasic sites in double stranded DNA, however, some have the ability to target abasic sites in ssDNA. Other methods of cleaving the DNA substrate after it is modified by the RIP are possible, which include but are not limited to using sodium hydroxide, putrescine dihydrochloride, and aniline, among others.

At step 16 of the method, cleavage of the substrate with an abasic site by the AP lyase or other separation method allows the fluorophore located on, at, or in proximity to one end of the substrate molecule and a quencher located on, at, or in proximity to the opposite or another end of the substrate molecule to separate from one another. See, for example, FIG. 4.

At step 18, as the fluorophore and quencher separate from one another, the quenching effects of the quencher diminish and the fluorophore can emit a fluorescent signal. The fluorescent signal can then be detected, which indicates the presence of a RIP in the sample.

Figure 7:
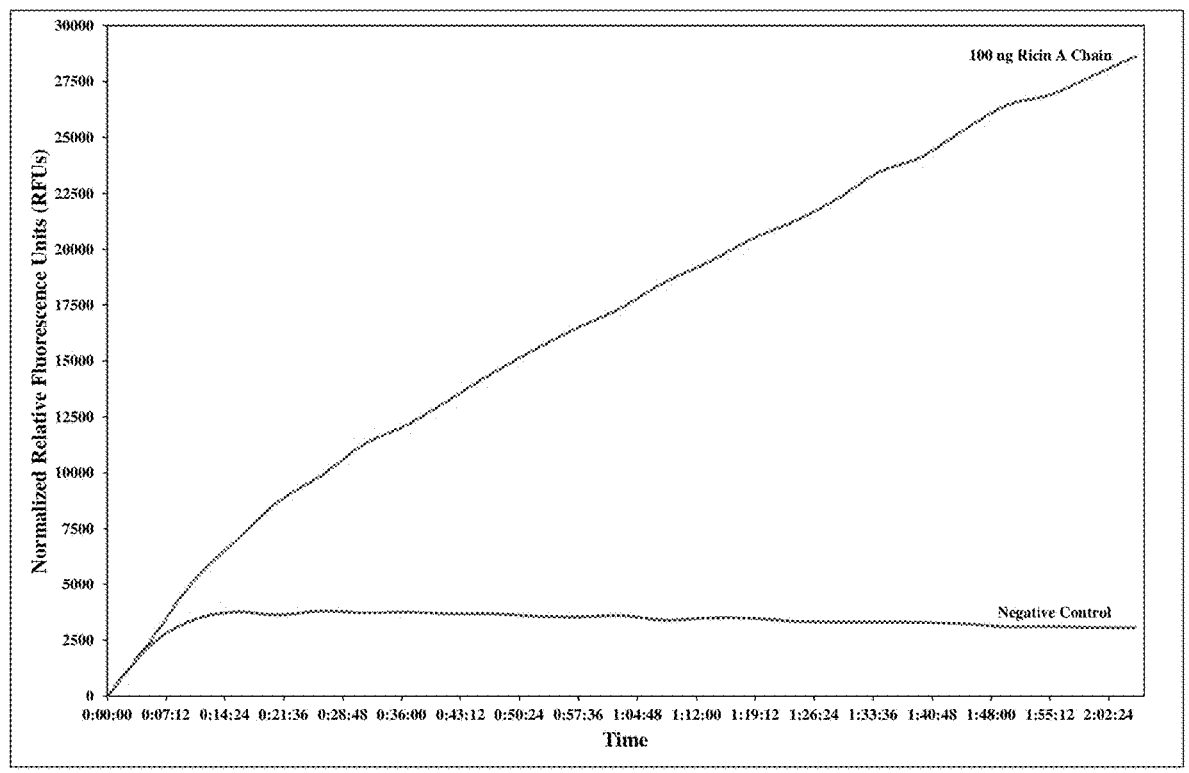

Initial assay development was conducted in the FilterMax® F5 fluorometer because it is temperature controlled (from 25° C.-45° C.) and can precisely detect changes in fluorescence over time with multiple readings taken at regular intervals. Currently, the assay is optimized to detect ricin A chain activity under the following conditions: 40 mM citric acid-sodium citrate buffer pH 4.0, 500 nM substrate (Table 1), 10 units of Endonuclease VIII, and incubated at 37° C. Typically, studies were performed using 50 µL reaction volumes in the FilterMax® F5 fluorometer and run for 2 hours at 37° C. with readings taken at 1 minute intervals. FIG. 7 is a graphical representation of ricin A chain activity using SEQ. ID NO. 1 and 100 ng of ricin A chain as detected in the FilterMax® F5 fluorometer.

Figure 8:
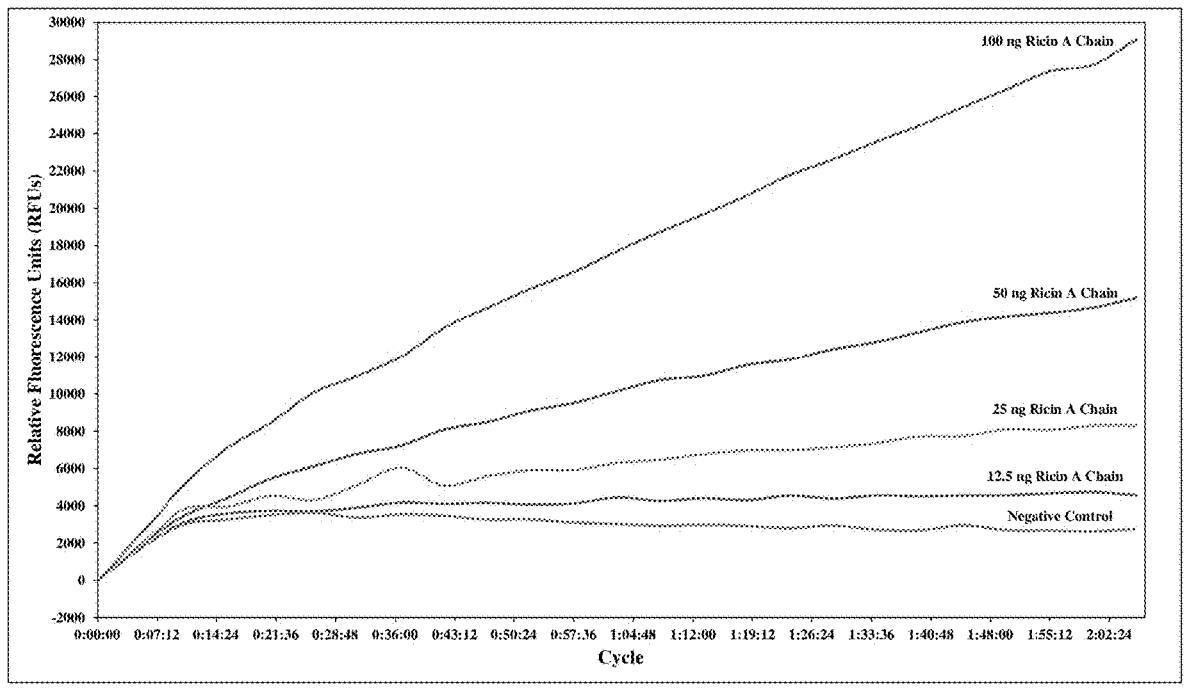

To determine the limit of detection of the ricin assay in the FilterMax® F5 fluorometer, 500 nM SEQ. ID NO. 1 was incubated in 50 µL reactions with the following amounts of ricin A chain: 12.5 ng, 25 ng, 50 ng, and 100 ng. The reaction conditions also included 40 mM citric acid-sodium citrate buffer pH 4.0 and 10 units of Endonuclease VIII, and was incubated at 37° C. for 2 hours with fluorescence readings taken at 1 minute intervals. FIG. 8 is a graphical representation of a limit of detection study for ricin A chain performed in the FilterMax® F5 fluorometer. The current limit of detection for the ricin assay using SEQ. ID NO. 1 is 12.5 ng of ricin A chain.

Figure 9:
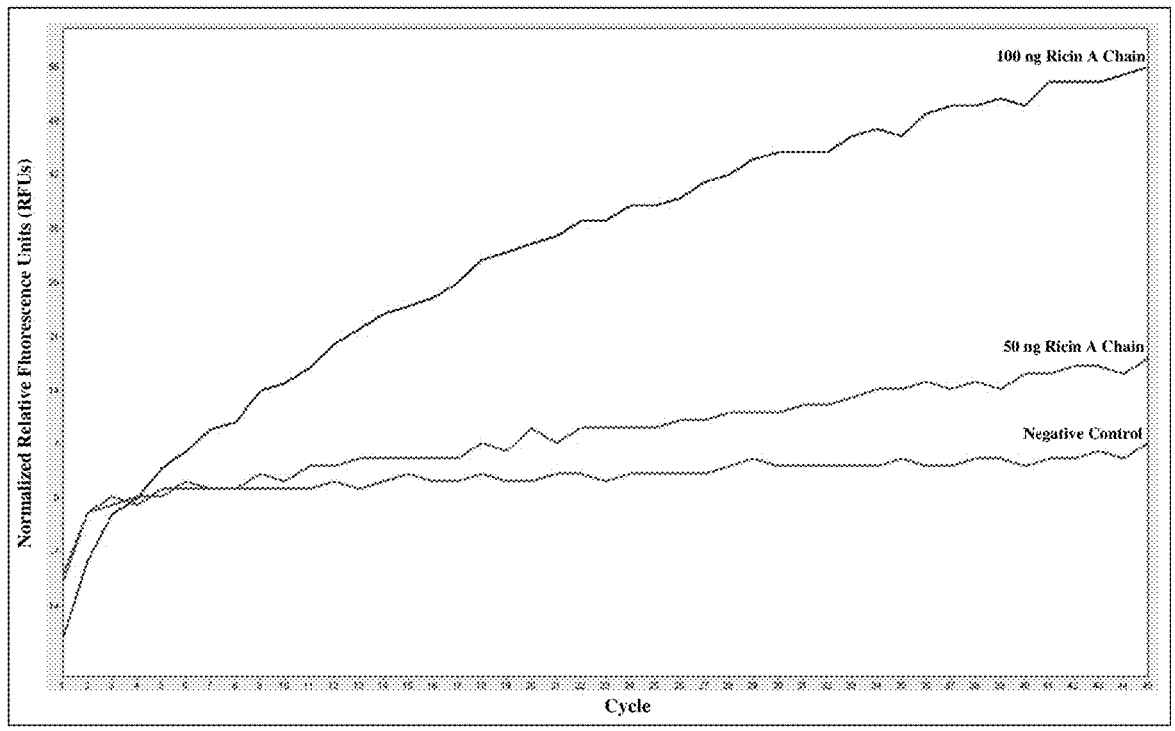

According to one embodiment is a fieldable assay for the detection of Ricin and/or other RIPs using an instrument capable of measuring fluorescence. A fluorescence-based enzyme activity assay can be analyzed using a variety of instruments, including real time quantitative polymerase chain reaction (qPCR) platforms. Real time qPCR is a very sensitive and quick method for detecting biological organisms by amplifying specific regions of genomic deoxyribonucleic acid (gDNA) and can be used to detect the genes coding for toxins produced by organisms. Real time qPCR instruments provide the advantage of detecting full organism biological threats in addition to detecting the activity of protein toxins. The RIP-detection methods described herein, for example, could use the RAZOR™ EX, produced by Idaho Technology, Inc. (Salt Lake City, Utah) for detection and analysis. The RAZOR™ EX is a qPCR-based platform that has the ability to detect fluorescence and is commonly used in biodefense. This instrument is ideal because it is a ruggedized platform designed for field use and it can yield results in less than 1 hour. In order to perform the assay on the RAZOR™ EX, an isothermal cycling protocol created to heat to 37° C. was applied (for more information about the cycling protocol, see U.S. Provisional Application No. 61/732,436, filed on Dec. 3, 2012, the entire contents of which are hereby incorporated by reference). The typical reactions for the ricin detection assay were carried out in a 12×1 pouch (200 µL volume per well containing 40 mM citric acid-sodium citrate buffer pH 4.0, 500 nM SEQ. ID NO. 2, and 10 units of Endonuclease VIII). The reactions were incubated at 37° C. for 45 minutes, with fluorescence readings taken at 1 minute intervals. FIG. 9 is a graphical representation of ricin A chain activity using SEQ. ID NO. 2 as detected in the RAZOR™ EX instrument. The low pH of the buffer system (40 mM citric acid-sodium citrate buffer pH 4.0) causes a decrease in fluorescence intensity emitted by the 6FAM™ fluorophore, which is consequently undetectable due to the lower sensitivity of the RAZOR™ EX instrument. Therefore, SEQ. ID NO. 2 was synthesized using the sequence from SEQ ID NO. 1 and the fluorophore Alexa Fluor® 488, which is unaffected by changes in pH. Therefore, SEQ. ID NO. 2 allows for the activity of ricin A chain to be detected in the RAZOR™ EX. More sensitive instruments, such as the FilterMax® F5 fluorometer, can detect ricin A chain activity in substrates using the 6FAM™ fluorophore.

Therefore, according to one embodiment, ricin or another RIP will remove an adenine from a labeled DNA substrate (including, but not limited to, a ssDNA substrate) thereby creating an abasic site. An AP lyase will then cleave the DNA substrate at the abasic site, thereby allowing the fluorophore at one end of the DNA substrate and the quencher at the other end of the DNA substrate to spatially separate. Once the fluorophore and the quencher are sufficiently separated, the fluorophore will emit a fluorescence signal. Increasing fluorescence, indicating Ricin activity, will be monitored in real time using a detection system such as a qPCR system.

Figure 10:
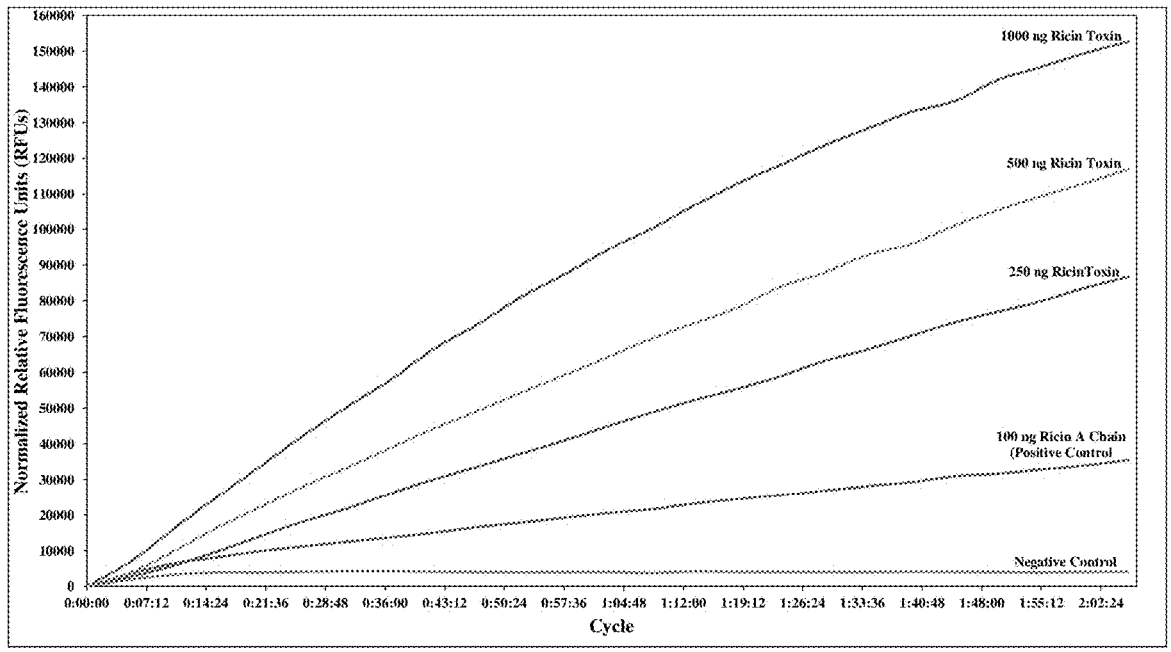

Embodiments of the present invention were validated using the ricin holotoxin in the FilterMax® F5 fluorometer using SEQ. ID NO. 1. The same experimental conditions that were used for ricin A chain detection were used for the ricin holotoxin studies: 50 µL volume per well containing 40 mM citric acid-sodium citrate buffer pH 4.0, 500 nM SEQ. ID NO. 1, and 10 units of Endonuclease VIII. The assay was incubated at 37° C. for 2 hours, with fluorescence readings taken at 1 minute intervals. Three different amounts of ricin holotoxin were tested, 250 ng, 500 ng, and 1000 ng. FIG. 10 is a graphical depiction of ricin holotoxin activity.

Figure 11:
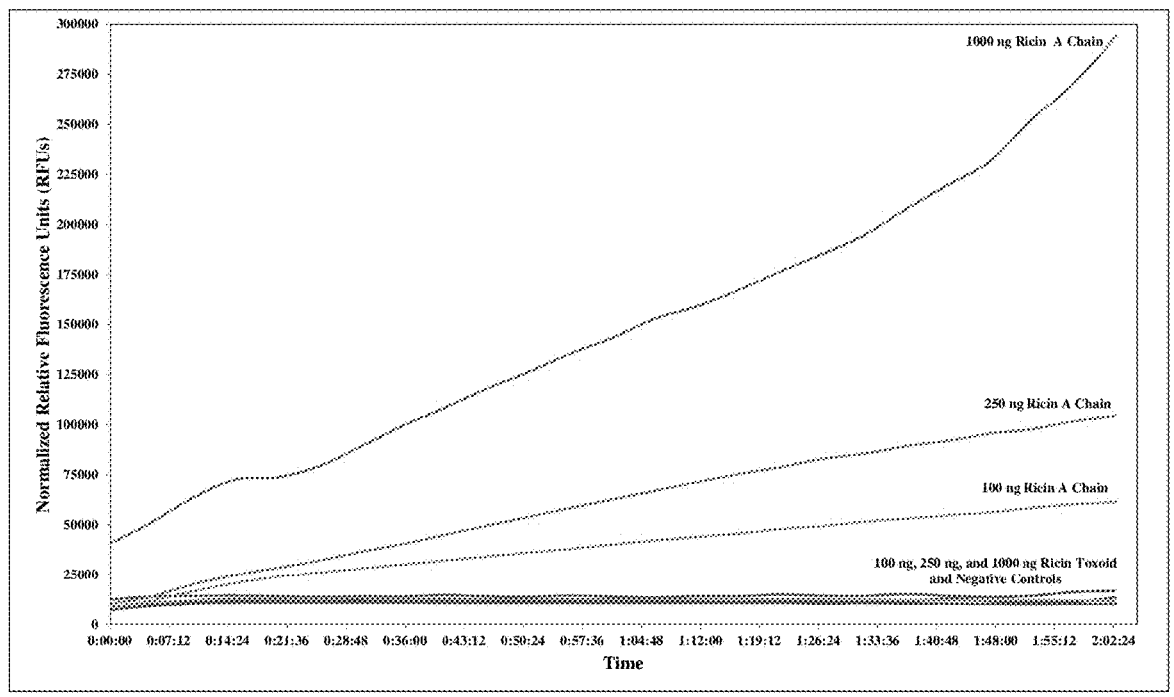

Since one goal is to design an assay capable of detecting only the biologically active form of ricin/RIPs. Therefore, a version of ricin known to be chemically inactivated (ricin toxoid) was assessed in a study with SEQ. ID NO. 1 in the FilterMax® F5 fluorometer. FIG. 11 is a graphical representation of ricin toxoid activity in comparison to ricin A chain activity. 1000 ng, 250 ng, and 100 ng of each ricin toxoid and ricin A chain were tested in the following conditions: 50 µL volume per well containing 40 mM citric acid-sodium citrate buffer pH 4.0, 500 nM SEQ. ID NO. 1, and 10 units of Endonuclease VIII. The assay was incubated at 37° C. for 2 hours, with fluorescence readings taken at 1 minute intervals. The results from this experiment show that increasing ricin A chain amounts gave increasing fluorescence readings, while the ricin toxoid at any of the amounts tested did not give an increase in fluorescence signal. Therefore, the inactive form of the ricin toxin was not detected because it was not enzymatically active.

According to one embodiment is provided a kit for the detection of a RIP in a sample. The kit could include a minimal complement of components such as the substrate. Alternatively, the kit could include, but is not limited to, the AP lyase and/or a qPCR detection system.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

---

What is claimed is:

1. A method for determining whether an unknown sample includes a ribosome inactivating protein, comprising the steps of:
   providing a reaction mixture containing an apurinic/apyrimidinic (AP) lyase and a nucleic acid substrate having a fluorophore attached to a first end of the substrate, a quencher attached to a second end of the substrate, and a region in the substrate between the first end and the second end that will form an abasic site in the presence of a ribosome inactivating protein, wherein the nucleic acid substrate is selected from the group consisting of SEQ. ID NO. 1, SEQ. ID NO. 2, SEQ. ID NO. 3, SEQ. ID NO. 4, SEQ. ID NO. 5, SEQ. ID NO. 6, SEQ. ID NO. 7, SEQ. ID NO. 8, SEQ. ID NO. 9, SEQ. ID NO. 10, SEQ. ID NO. 11, and SEQ. ID NO. 12;
   adding the unknown sample to the reaction mixture;
   incubating the unknown sample in the reaction mixture such that any ribosome inactivating protein in the unknown sample will form the abasic site in the nucleic acid substrate and the AP lyase will cleave the nucleic acid substrate at the abasic site; and
   measuring any fluorescence from the sample to determine whether the sample includes ribosome inactivating protein.

2. The method of claim 1, wherein said ribosome inactivating protein is ricin.

3. The method of claim 1, wherein the nucleic acid substrate is selected from the group consisting of: dsDNA, ssDNA, RNA, oligonucleotides, chimeric nucleic acids, and combinations thereof.

4. The method of claim 1, wherein said region in the substrate comprises a sarcin-ricin loop.

5. A method for determining whether an unknown sample includes a ribosome inactivating protein, comprising the steps of:
   providing a reaction mixture containing an apurinic/apyrimidinic (AP) lyase and a nucleic acid substrate having a fluorophore attached to a first end of the substrate, a quencher attached to a second end of the substrate, and a region in the substrate between the first end and the second end that will form an abasic site in the presence of a ribosome inactivating protein;
   adding the unknown sample to the reaction mixture;
   incubating the unknown sample in the reaction mixture such that any ribosome inactivating protein in the unknown sample will form the abasic site in the nucleic acid substrate and the AP lyase will cleave the nucleic acid substrate at the abasic site; and
   measuring any fluorescence from the sample to determine whether the sample includes ribosome inactivating protein;
   wherein the AP lyase is Endonuclease VIII.

* * * * *

SEQUENCE LISTING

```
<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: oligonucleotide

<400> SEQUENCE: 1
atgcagcagc agagagaagc aattcgt                                              27

<210> SEQ ID NO 2
<211> LENGTH: 27
<212> TYPE: DNA
<213> ORGANISM: Artificial sequence
<220> FEATURE:
<223> OTHER INFORMATION: oligonucleotide

<400> SEQUENCE: 2
atgcagcagc agagagaagc aattcgt                                              27

<210> SEQ ID NO 3
<211> LENGTH: 27
<212> TYPE: DNA
<213> ORGANISM: Artificial sequence
<220> FEATURE:
<223> OTHER INFORMATION: oligonucleotide

<400> SEQUENCE: 3
acgaattgct tctctctgct gctgcat                                              27

<210> SEQ ID NO 4
<211> LENGTH: 27
<212> TYPE: DNA
<213> ORGANISM: Artificial sequence
<220> FEATURE:
<223> OTHER INFORMATION: oligonucleotide

<400> SEQUENCE: 4
atgcagcagc aggggggaagc aattcgt                                             27

<210> SEQ ID NO 5
<211> LENGTH: 28
<212> TYPE: DNA
<213> ORGANISM: Artificial sequence
<220> FEATURE:
<223> OTHER INFORMATION: oligonucleotide

<400> SEQUENCE: 5
atgcatgcag cagagagaag caattcgt                                             28

<210> SEQ ID NO 6
<211> LENGTH: 26
<212> TYPE: DNA
<213> ORGANISM: Artificial sequence
<220> FEATURE:
<223> OTHER INFORMATION: oligonucleotide

<400> SEQUENCE: 6
```

```
aaaaaaaaaa agagaaaaaa aaaaaa                                          26

<210> SEQ ID NO 7
<211> LENGTH: 26
<212> TYPE: DNA
<213> ORGANISM: Artificial sequence
<220> FEATURE:
<223> OTHER INFORMATION: oligonucleotide

<400> SEQUENCE: 7
aaaaaaagaa agagattaca aaaaaa                                          26

<210> SEQ ID NO 8
<211> LENGTH: 26
<212> TYPE: DNA
<213> ORGANISM: Artificial sequence
<220> FEATURE:
<223> OTHER INFORMATION: oligonucleotide

<400> SEQUENCE: 8
aaaaaaaaaa ggagactaaa aaaaaa                                          26

<210> SEQ ID NO 9
<211> LENGTH: 26
<212> TYPE: DNA
<213> ORGANISM: Artificial sequence
<220> FEATURE:
<223> OTHER INFORMATION: oligonucleotide

<400> SEQUENCE: 9
atgcctccag cagagaagca attcgt                                          26

<210> SEQ ID NO 10
<211> LENGTH: 27
<212> TYPE: DNA
<213> ORGANISM: Artificial sequence
<220> FEATURE:
<223> OTHER INFORMATION: oligonucleotide

<400> SEQUENCE: 10
tgctcctagt acgagaggac cggagtg                                         27

<210> SEQ ID NO 11
<211> LENGTH: 27
<212> TYPE: DNA
<213> ORGANISM: Artificial sequence
<220> FEATURE:
<223> OTHER INFORMATION: oligonucleotide

<400> SEQUENCE: 11
atgcagcagc agugagaagc aattcgt                                         27

<210> SEQ ID NO 12
<211> LENGTH: 31
<212> TYPE: DNA
<213> ORGANISM: Artificial sequence
<220> FEATURE:
<223> OTHER INFORMATION: oligonucleotide

<400> SEQUENCE: 12
cctgctagca gacgagagga gcaattgctt g                                    31
```